(12) United States Patent
Aharonov et al.

(10) Patent No.: US 7,393,589 B2
(45) Date of Patent: Jul. 1, 2008

(54) DUAL LAYER DIFFUSION BONDED CHEMICAL VAPOR COATING FOR MEDICAL IMPLANTS

(75) Inventors: Robert Aharonov, W. Bloomfield, MI (US); Raymond Fontana, Waldwick, NJ (US)

(73) Assignee: Ionbond, Inc., Madison Heights, MI (US)

( * ) Notice: Subject to any disclaimer, the term of this patent is extended or adjusted under 35 U.S.C. 154(b) by 0 days.

(21) Appl. No.: 11/046,311

(22) Filed: Jan. 28, 2005

(65) Prior Publication Data

US 2005/0191408 A1 Sep. 1, 2005

Related U.S. Application Data

(60) Provisional application No. 60/540,927, filed on Jan. 30, 2004.

(51) Int. Cl.
*B32B 9/00* (2006.01)
(52) U.S. Cl. .................. 428/469; 428/472; 428/698; 428/701; 428/702
(58) Field of Classification Search .................. None
See application file for complete search history.

(56) References Cited

U.S. PATENT DOCUMENTS

| | | | |
|---|---|---|---|
| 4,687,487 A | 8/1987 | Hintermann | 623/18 |
| 4,904,634 A * | 2/1990 | Wieserman et al. | 502/401 |
| 5,037,438 A | 8/1991 | Davidson | 623/18 |
| 5,180,394 A | 1/1993 | Davidson | 623/18 |
| 5,702,448 A | 12/1997 | Buechel et al. | 623/16 |
| 5,868,796 A | 2/1999 | Buechel et al. | 623/16 |
| 6,261,322 B1 | 7/2001 | Despres, III et al. | 623/23.53 |

(Continued)

OTHER PUBLICATIONS

Hayashi, K., Matsuguchi, N., Uenoyama, K., Kanemaru, T., Sugioka, Y., Evaluation of metal implants coated with several types of ceramics as biomaterials. Journal of Biomedical MAterials Research, vol. 23, 1247-1259 (1989).

(Continued)

*Primary Examiner*—Jennifer McNeil
*Assistant Examiner*—Timothy M Speer
(74) *Attorney, Agent, or Firm*—Gifford Krass Sprinkle Anderson & Citkowski, P.C.

(57) ABSTRACT

Coatings for use in artificial joints and other implanted medical devices. The coatings comprise a dual layer structure vapor deposited atop a medical grade substrate, such as cobalt chromium. The dual layer structure comprises a first ceramic layer vapor deposited atop at least a portion of the substrate and a second ceramic layer deposited atop the first ceramic layer. The first ceramic layer is formed of a material which has particularly good adhesion to the substrate, and the second ceramic layer from a material exhibiting particularly high hardness and good wear characteristics. The vapor deposition process is controlled so as to form a graded interface between the two ceramic layers to form a dual layer coating which resists delamination, adheres well to the substrate, and exhibits good wear characteristics in situ.

27 Claims, 10 Drawing Sheets

U.S. PATENT DOCUMENTS

| | | | |
|---|---|---|---|
| 6,548,104 B2 | 4/2003 | Pappas | 427/2.26 |
| 6,596,225 B1 | 7/2003 | Pope et al. | 419/11 |
| 7,048,792 B2 * | 5/2006 | Axen et al. | 106/692 |
| 2001/0036530 A1 * | 11/2001 | Noda et al. | 428/104 |
| 2002/0018851 A1 * | 2/2002 | Chang et al. | 427/299 |

OTHER PUBLICATIONS

Davidosn, Ph.D. J.A., Mishra, Ph.D. A.K., Surface Modification Issues for Orthopaedic Implant Bearing Surfaces. Orthopaedic Research Department Smith and Nephew Richards Inc. Proc. 5th International Conference on Surface Modification Technologies, Birmingham, U.K., Sep. 2-4, 1991.

Coll, B., Jacquot, P. Surface Modification of Medical Implants and Surgical Devices Using Tin layers, Surface and Coatings Technology, 36 (1988) 867-878.

Davidson, Ph.D., J.A. Chracteristics of Metal and Ceramic Total Hip Bearing Surfaces and the Effect on Long-Term UHMWPE Wear. Orthopaedic Research Department Smith and Nephew Richards, Inc. OR-92-08 Jan. 14, 1992.

* cited by examiner

DUAL LAYER DIFFUSION BONDED CHEMICAL VAPOR COATING FOR MEDICAL IMPLANTS

RELATED APPLICATION

This patent application claims priority of U.S. Provisional Patent Application Ser. No. 60/540,927 filed Jan. 30, 2004 entitled "Dual Layer Diffusion Bonded Chemical Vapor Coating for Medical Implants," which is incorporated herein by reference.

FIELD OF THE INVENTION

This invention concerns the field of coated medical implants, and more specifically, the field of vapor depositing a dual layered ceramic structure atop a medical implant substrate.

DESCRIPTION OF THE RELEVANT PRIOR ART

In recent years, more and more patients have received medical implants, such as hip, knee and shoulder prostheses. Generally speaking, if these prostheses are to function properly in an active human being, they must be comprised of a biologically compatible, lightweight and strong material. Typically, these prostheses materials include stainless steel, cobalt-chrome, or titanium alloy.

While such prostheses and prosthetic components have worked relatively well, they do have certain problems. For example, issues of tissue compatibility can arise, and particularly when the prosthetic components are used to fashion joints because the action of flexing a knee, hip or shoulder causes the metallic components to slide and rub across each other (articular contact) and this is known to produce molecular and chemical reactions that generate wear, and debris, and degrade the performance of the prosthetic joint. Furthermore, some of the byproducts generated from the articular contact are suspected to cause tissue damage and adverse biological reactions leading to the subsequent loosening of the implant device.

Accordingly, a number of coatings have been developed to improve the performance characteristics of medical implants and prostheses. Examples of such coatings include those in which a ceramic layer is disposed atop a metal alloy. For example, U.S. Pat. Nos. 5,868,796 and 5,702,448 both disclose plasma arc deposited ceramic coatings on medical implants. Specific ceramic or carbon-based materials disclosed include TiN, TiB, and $Al_2O_3$, as well as zirconia or diamond-like carbon (DLC). Both of these patents disclose single layer ceramic coatings. U.S. Pat. No. 6,261,322 discloses a structured surface formed on the metallic substrate and an osteoconductive coating deposited on the structured surface. The structured surface is defined by a material that includes a plurality of particles that are sintered together to form a continuous porous phase. The coating can be formed by physical vapor deposition (PVD) or chemical vapor deposition (CVD). U.S. Pat. No. 6,548,104 discloses implants having TiN coatings deposited by a plasma arc process. U.S. Pat. Nos. 5,037,438 and 5,180,394 disclose implant systems comprised of zirconium alloy substrates having coatings of zirconium oxide or nitride thereupon. U.S. Pat. No. 6,596,225 discloses implants coated with diamond-like carbon. U.S. Pat. No. 4,687,487 discloses implants coated with oxides, oxynitrides, carbon nitrites, and oxycarbon nitrites of titanium.

Prior art coatings such as those discussed above have been known to suffer a variety of shortcomings, particularly when the prostheses are used over a prolonged period of time. The coatings can lack sufficient adherence to stay in place over time. They often do not have sufficiently high hardness and wear-resistance characteristics and eventually wear through to the underlying substrate material. Furthermore, they may not wear smoothly and may produce increasing friction as time goes on. Accordingly, there still exists a need for prosthetic devices which have a biologically compatible coating extremely adherent to the underlying substrate, yet with an exposed surface which has sufficiently high hardness and wear characteristics to last the lifetime of the implant patient.

SUMMARY OF THE INVENTION

The present invention has been developed to overcome the problems in the prior art discussed above. The invention is a medical implant which is coated with a unique multi-layer ceramic structure having a graded interface between two ceramic layers having different performance characteristics. The invention also includes a coating suitable for use on a biologically compatible prosthetic substrate, as well as a method of vapor depositing the coating on the substrate.

In its broadest aspect, the coating of the present invention is a vapor deposited coating having a dual layered structure comprised of a first ceramic layer deposited atop at least a portion of the substrate, and a second ceramic layer deposited atop an upper surface of the first ceramic layer. The vapor deposition process is controlled so as to produce a more accurate diffusion bonded, graded interface between the first layer and the substrate and the two ceramic layers.

Preferably, the first ceramic layer is selected so as to have exceptionally good adherence to an underlying substrate comprised of a biologically compatible metallic alloy, such as cobalt-chromate. While high hardness and wear characteristics are also desirable in the material used to form the first ceramic layer, the emphasis is primarily on the high adherence characteristic. In the present invention the adherence is achieved by the proper selection and control of the vapor deposition process and the coating to create a diffusion bonding. In contrast, the second ceramic layer is selected from a material which has high hardness and good wear characteristics. Since this layer will not be deposited directly on the substrate, adherence to the substrate is not important. Of course, the second layer must adhere to the first layer, and this is achieved in the process of the present invention by controlling the vapor deposition of the two layers such that a graded interface is created between them. In this way, the second ceramic layer adheres extremely well to the first ceramic layer.

In a preferred embodiment of the present invention, the first ceramic layer is formed of titanium nitride (TiN) and the second ceramic layer is formed of aluminum oxide ($Al_2O_3$).

In another preferred embodiment, the first ceramic layer has a thickness which is substantially greater than, equal to or less than a thickness of the second ceramic layer. In a particularly preferred embodiment, the first thickness is in the range of approximately 3-15 micrometers, and the second thickness is in the range of approximately 0.5-25 micrometers.

Preferably, after the multi-layer coating is deposited on the substrate, the exposed surface of the second ceramic layer is polished to achieve the proper surface before being implanted in a patient.

BRIEF DESCRIPTION OF THE DRAWINGS

The following detailed description may best be understood by reference to the following drawings, in which.

DETAILED DESCRIPTION OF THE PREFERRED EMBODIMENTS

Throughout the following detailed description, like numerals are used to reference like elements of the invention shown on multiple figures thereof.

Figure 1:
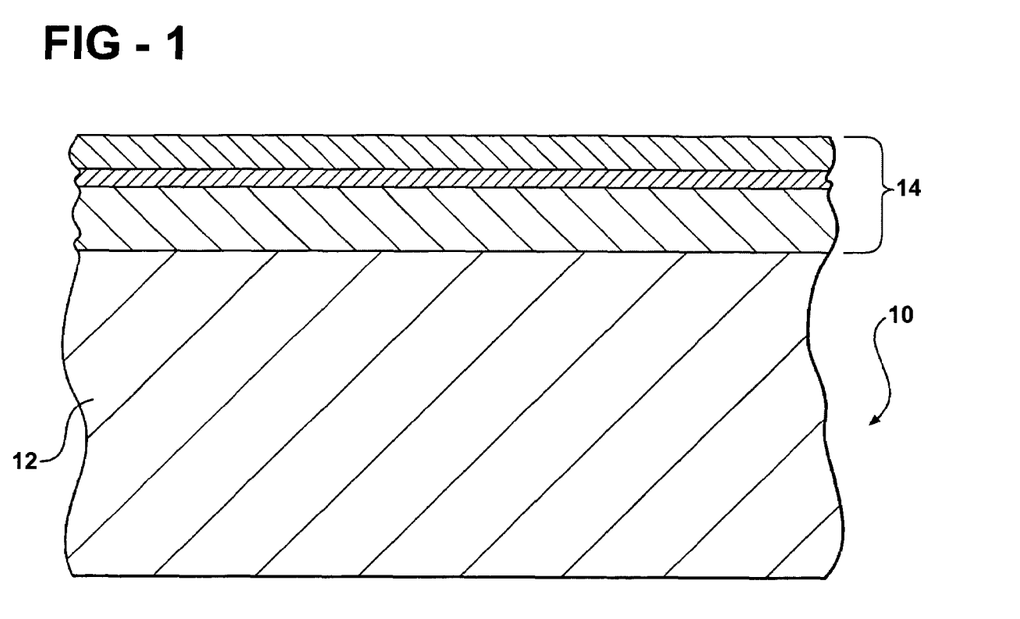
FIG. 1 is a cross-sectional view of a medical implant coated with the multi-layer coating of the present invention.

Referring now to the drawings, FIG. 1 depicts in cross-section a portion of a medical implant 10 coated with the dual layered structure 14 of the present invention. The medical implant 10 comprises a substrate 12 which may be formed of any biologically compatible material suitable for this purpose, such as carbon composite, stainless steel, cobalt chromium, titanium alloy, tantalum or ceramic materials, or combinations thereof. In a particularly preferred embodiment, the substrate 12 is formed of cobalt chromium (CoCr) medical grade alloy. However, the particular choice of substrate is not considered critical to the practice of the present invention provided that it meets the requirements for biocompatibility and the deposition process.

Vapor deposited atop at least portions of substrate 12 is a dual layered structure 16 that includes a first ceramic layer 18. Preferably, the first ceramic layer 18 is selected from a material highly adherent to the substrate 12. Vapor deposited atop the first ceramic layer 16 is a second ceramic layer 18 which is formed of a ceramic material different from the ceramic material of first layer 16. In particular, the material of second ceramic layer 18 is selected so as to have high hardness and wear characteristics. Of course, it is important that both ceramic layers 16 and 18 be adherent, hard, and have good wear characteristics, but the high adherence characteristic is of primary importance for first ceramic layer 16. The first ceramic layer is properly chosen to form a diffusion-bonded interface with the substrate, whereas the hardness and wear-resistant characteristics are of primary importance for second ceramic layer 18.

The ceramic layers 16, 18 are vapor deposited in such a fashion as to produce a graded interface 20 between the first and the second layers 16, 18. In other words, the composition of the graded interface 20 includes both the ceramic species of first ceramic layer 16, as well as the ceramic species of second ceramic layer 18. By carefully controlling the deposition process, the graded interface is diffusion bonded to both first and second ceramic layers 16, 18. Accordingly, there is no abrupt transaction between the two ceramic layers and excellent adherence is achieved.

In a particularly preferred embodiment, the first ceramic layer is formed of titanium carbonitride (TiCN). By experimentation, the present inventors have found that titanium carbonitride is particularly adherent to a medical implant substrate such as cobalt chromium and may be effectively vapor deposited on the substrate. Preferably, the first ceramic layer 16 has a thickness in the range of 3 to 50 micrometers, and typically a thickness of 5 to 20 micrometers.

In another particularly preferred embodiment, the second ceramic layer is formed of aluminum oxide ($Al_2O_3$). Through experimentation, it has been found that aluminum oxide exhibits particularly high hardness as a vapor deposited layer, and also exhibits excellent wear characteristics. Moreover, it has been found that the vapor deposition of titanium carbonitride and aluminum oxide may be manipulated in such a fashion that it is possible to create a graded interface between them. Because of this graded interface, the two ceramic layers are not completely discreet and this has important ramifications for the performance of the coating of the present invention in situ. Over time, the coating of the present invention when deposited on a substrate to form a medical implant, according to the present invention, will be subject to years and even decades of the articular contact described in the background section. The constant wear and tear or articulation the prostheses is subjected to can cause separation of coatings from the substrate, or delamination of multi-layer coatings. Because the graded interface of the coating and medical implant of the present invention is diffusion bonded in both ceramic layers, there is a greatly reduced risk of such delamination over time.

The method of the present invention uses vapor deposition to form the claimed coating. Vapor deposition may be either physical or chemical vapor deposition. However, in a preferred embodiment of the method of the present invention, chemical vapor deposition (CVD) is used to produce the dual layer structure. CVD coatings are characterized as coatings that are deposited by a high-temperature process (greater than 900° C.). The process begins with a carrier gas and disassociates it into its constituents and then recombines the separate gas species with another reactive gas to deposit a coating of desired combination onto substrate materials. This process is commercially viable and capable of depositing a variety of coatings that are conductive and refractory. Among the coatings suitable for CVD are titanium nitride, titanium carbonitride, and aluminum oxide, although, of course many other materials may be deposited by CVD as well.

More recently, advances in chemical vapor deposition have been introduced to enable the coatings to be deposited at lower temperatures and with higher energy. These new coating process enhancements are usually referred to as plasma-assisted (PACVD), plasma-enhanced (PECVD), or plasma-activated (PACVD) chemical vapor deposition. Typical enhancements that are used to help disassociate the carrier gases and promote the reactions with the reactive gases in the plasma are radio frequency generators or power supplies, hot filaments which emit electrons, lasers which oblate the gases, and microwave systems which increase energy levels in the plasma. There are other process enhancements that can be incorporated and these are only examples.

Medical implant alloy systems are typically made of the alloys of cobalt chrome and titanium aluminum vanadium (Ti6Al4V). The Ti6Al4V refers to the composition of the metals in the alloy system (titanium with 6 percent aluminum and 4 percent vanadium). More recently, alloy systems of zirconium have been introduced and there are also systems of stainless steel that have been accepted. These various alloy systems are used to fabricate a variety of orthopedic implant devices and systems that are used commercially to replace similar systems in the body. Knees, hips, shoulders, fingers, and various other joints and bones have been replaced by these types of implant systems. All of these fall under the ambit of the present invention.

Three CVD coatings were deposited onto substrates made of medical grade CoCr alloy and were subjected to coating and substrate analysis. The substrate of FIG. 2A was coated with a titanium carbonitride coating (commercially available as Bernex® MP01). The substrate of FIG. 2B was coated with a combination of TiCN plus $Al_2O_3$ (a commercially available product sold as Bernax® HSA) coating. The substrate of FIG. 2C was coated with a similar titanium carbonitride/aluminum oxide combination, but in somewhat different proportions of (commercially available as Bernex® HSE) coating. All of the three substrates were polished on one side prior to analysis. Analysis was performed to determine the coating thickness, adhesion, friction-coefficient and substrate condition. All of the tests were carried out in the Materials Laboratory at the IonBond, LLC. Technology Center.

Figure 2A:
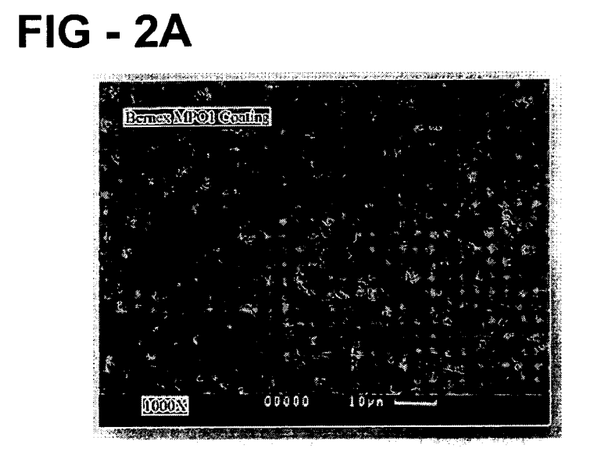
FIGS. 2A-2C are SEM micrographs showing the surface morphology of three chemically vapor-deposited coatings atop a cobalt chromium medical-grade alloy substrate.
Figure 2B:
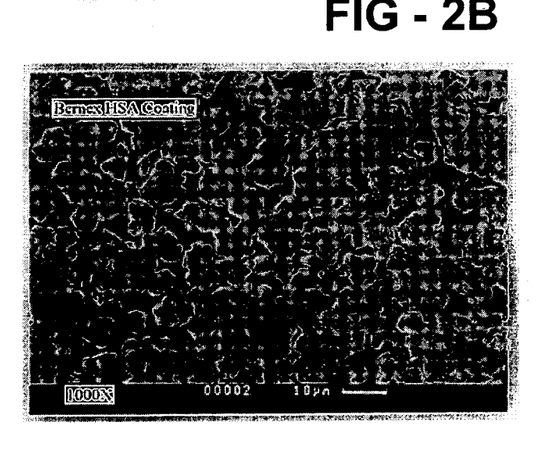
Figure 2C:
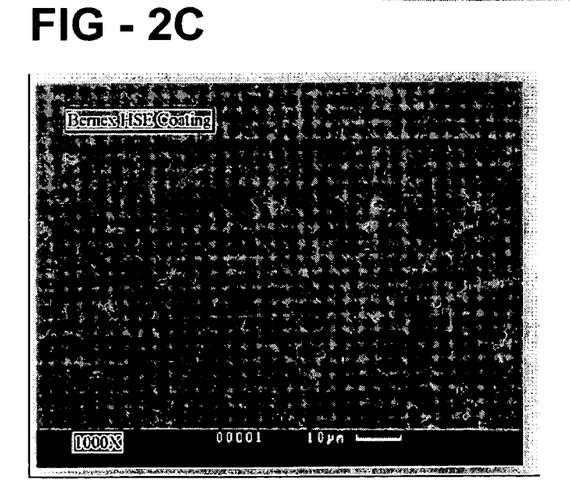

FIGS. 2A-2C are SEM micrographs which show the respective surface morphology of the three substrates, all at a magnification of 1,000×. As can be determined by visual inspection, the surface morphologies varied considerably, with the coating of FIG. 2B showing a somewhat coarser morphology than the other two coatings. However, all three surfaces looked typical of polished CVD coatings.

Rockwell hardness tests were performed on the three coatings. The coating of FIG. 3A had a hardness of 46.7 HRC. The coating of FIG. 2B displayed a hardness of 39.2 HRC, whereas the hardness exhibited by the coating of sample 2C was 40.6 HRC.

Figure 3A:
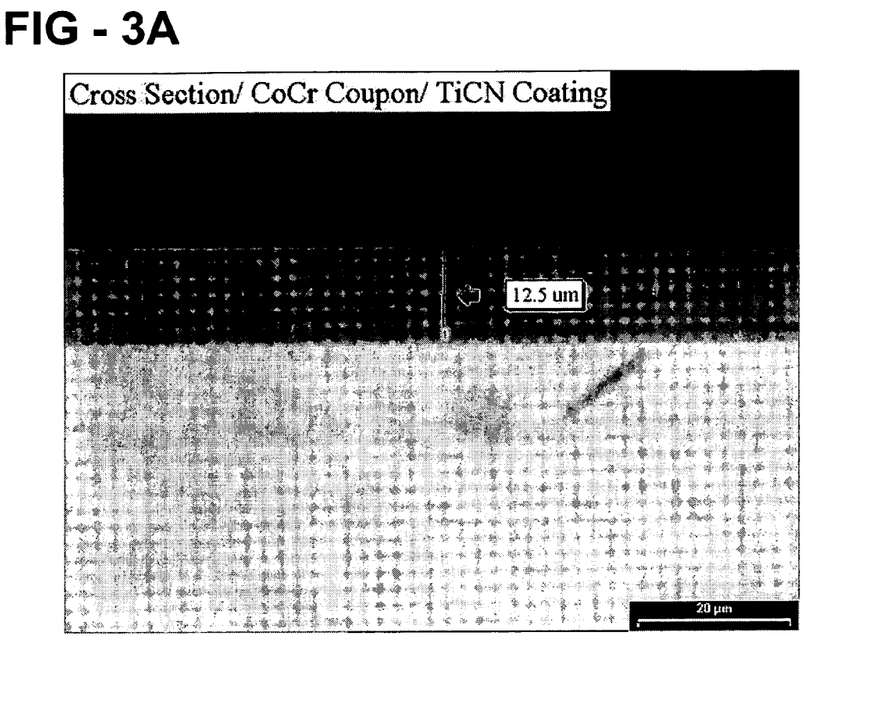
FIGS. 3A-3C are optical metallographs showing the respective cross-sections of the three coatings of FIGS. 2A-2C.
Figure 3B:
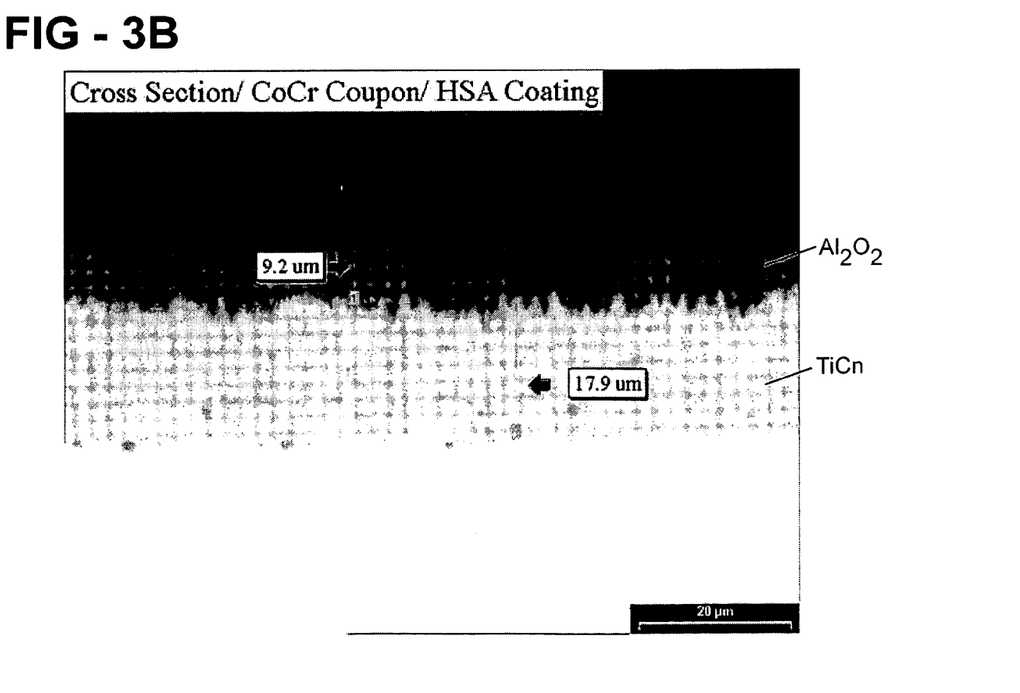
Figure 3C:
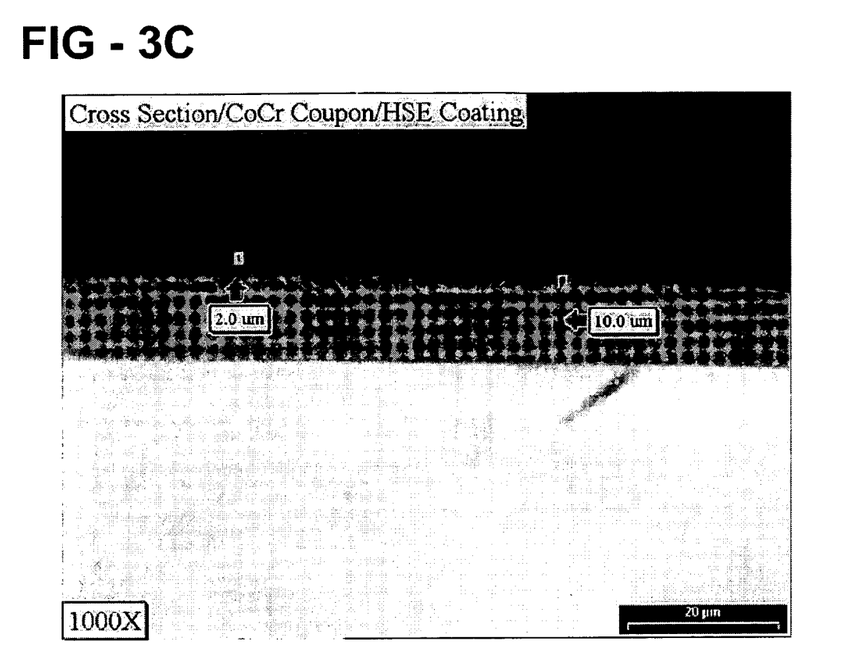

FIGS. 3A-3C are optical metallographs showing the respective cross-sections of the three coated substrates. The thickness of the coatings was measured by metallographic cross-sections. The coating of FIG. 3A (the titanium carbonitride coating) was approximately 13 micrometers thick. The two dual layered coatings of FIGS. 3B and 3C (titanium carbonitride/aluminum oxide) were approximately 27 micrometers and approximately 12 micrometers, respectively. As readily may be seen by examining the three metallographs and comparing the single specimen coating of FIG. 3A with the dual layer structure of FIGS. 3B and 3C, the addition of the aluminum oxide to the vapor deposition process has a profound effect on the structure of the coating. The single specimen titanium carbonitride coating of FIG. 3A is, as we would expect, a simple structure of consistently uniform appearance very well diffusion bonded to the substrate.

In contrast, the two titanium carbonitride/aluminum oxide coatings exhibit a much more complex structure. In each of them, we see a top darker layer of aluminum oxide and a lighter colored lower layer of titanium carbonitride deposited atop the substrate. These dual layers are, for the most part, uniform in structure throughout most of their respective thicknesses, but at their juncture, we see an irregular boundary. This photographic evidence strikingly shows how, by controlling the vapor deposition product of the two species used to form the coatings of FIGS. 3B and 3C, a graded interface between the two layers is produced which is comprised of both species in varying degrees. This interface between the first and second layers, upon closer examination, exhibits a toothed interlocking structure assuring optimal interlock and bonding between the two crystal systems. From this actual evidence, it can be readily understood how the dual layer structure of the coating and medical implant of the present invention resists delamination.

Figure 4A:
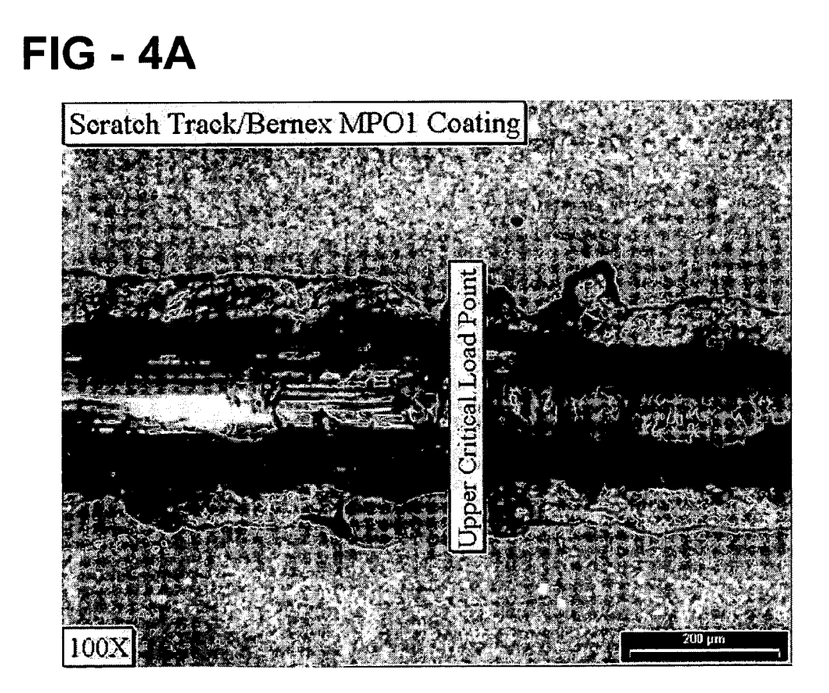
FIGS. 4A-4C are optical micrographs showing the respective scratch tracks of the coatings of FIGS. 2A-2C.
Figure 4B:
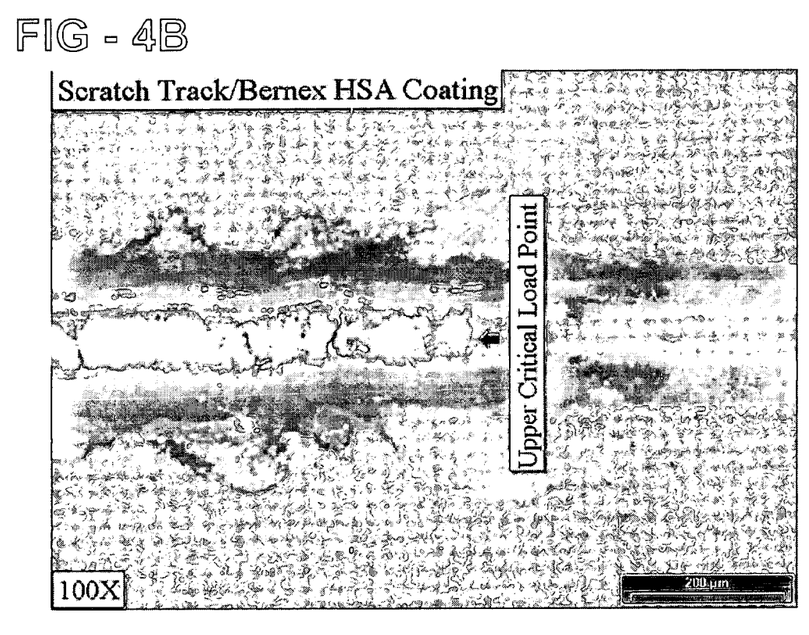
Figure 4C:
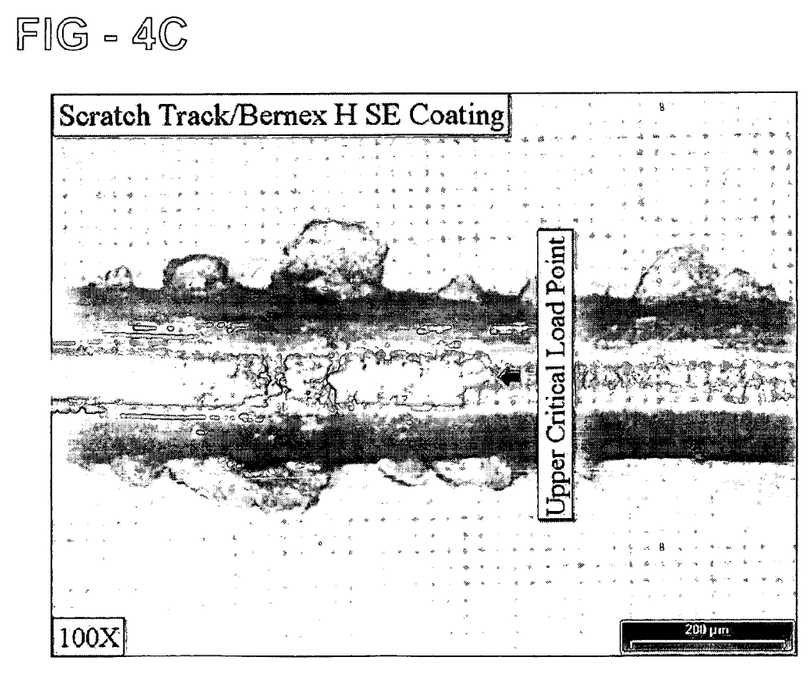

FIGS. 4A-4C are optical micrographs that show the respective scratch tracks of the three coated substrates. All three coatings displayed very good adhesion to the chromium cobalt substrate. This is not surprising because, in each of the three, the titanium carbonitride is deposited directly on the substrate. The upper critical load as measured by Scratch Test Method was greater than 100N. The coatings showed some minor cohesive spallations along the scratch near the end of the track. Mercedes tests of the coated substrates showed zero percent of the coatings falling around the indentation.

Figure 5A:
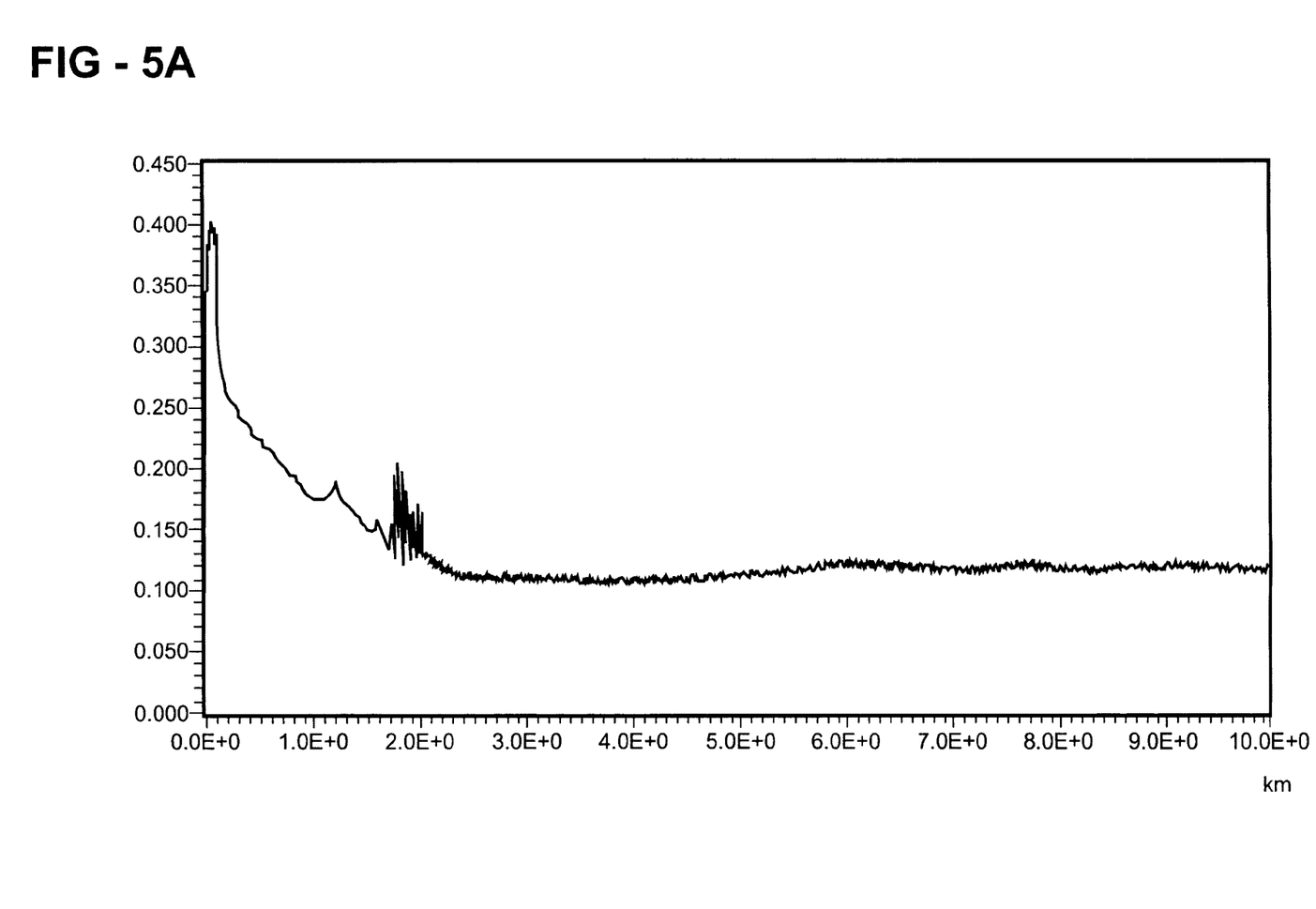
FIGS. 5A-5C are graphs depicting the friction coefficient versus distance curve, respectively, of the three coatings of FIGS. 2A-2C.
Figure 5B:
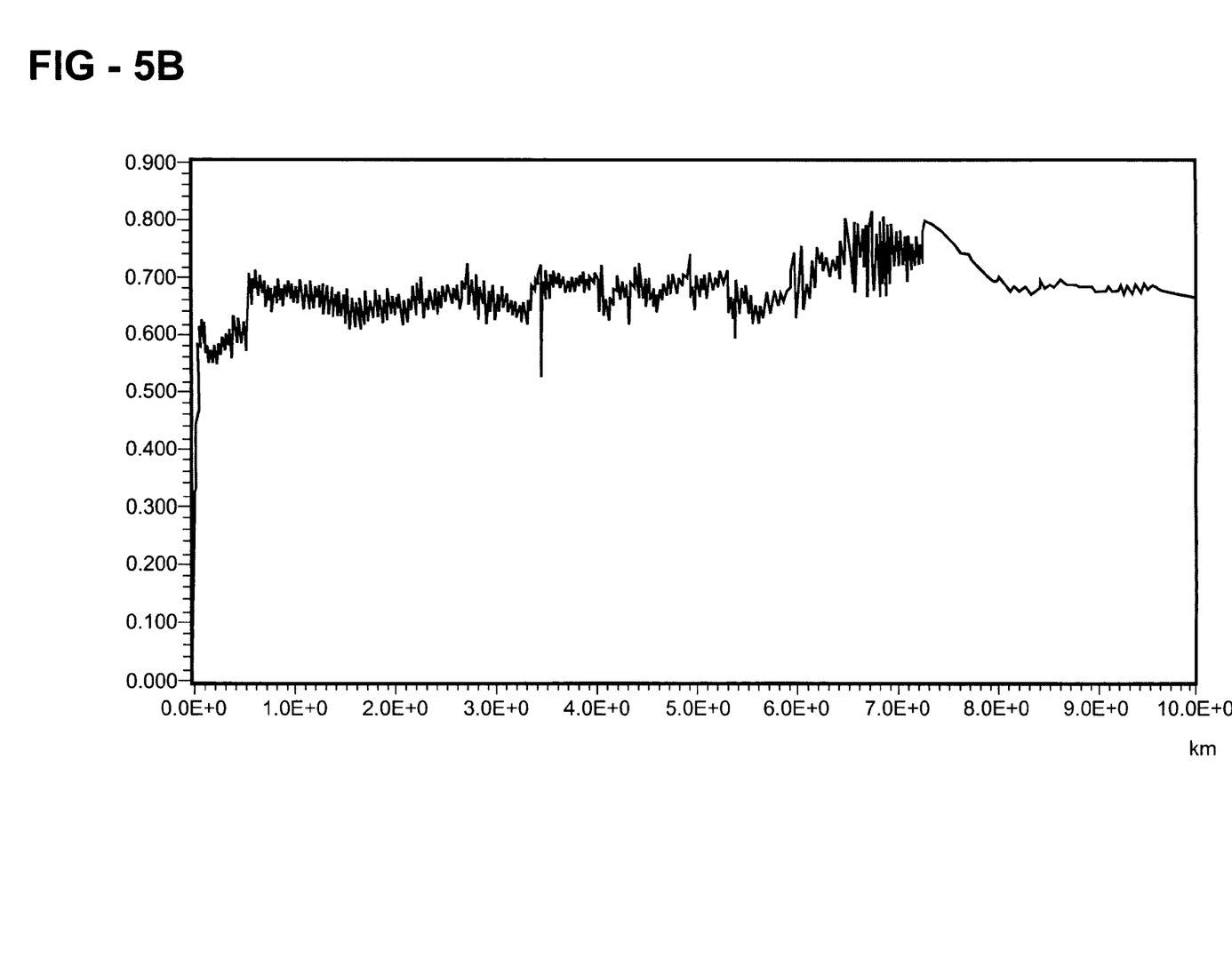
Figure 5C:
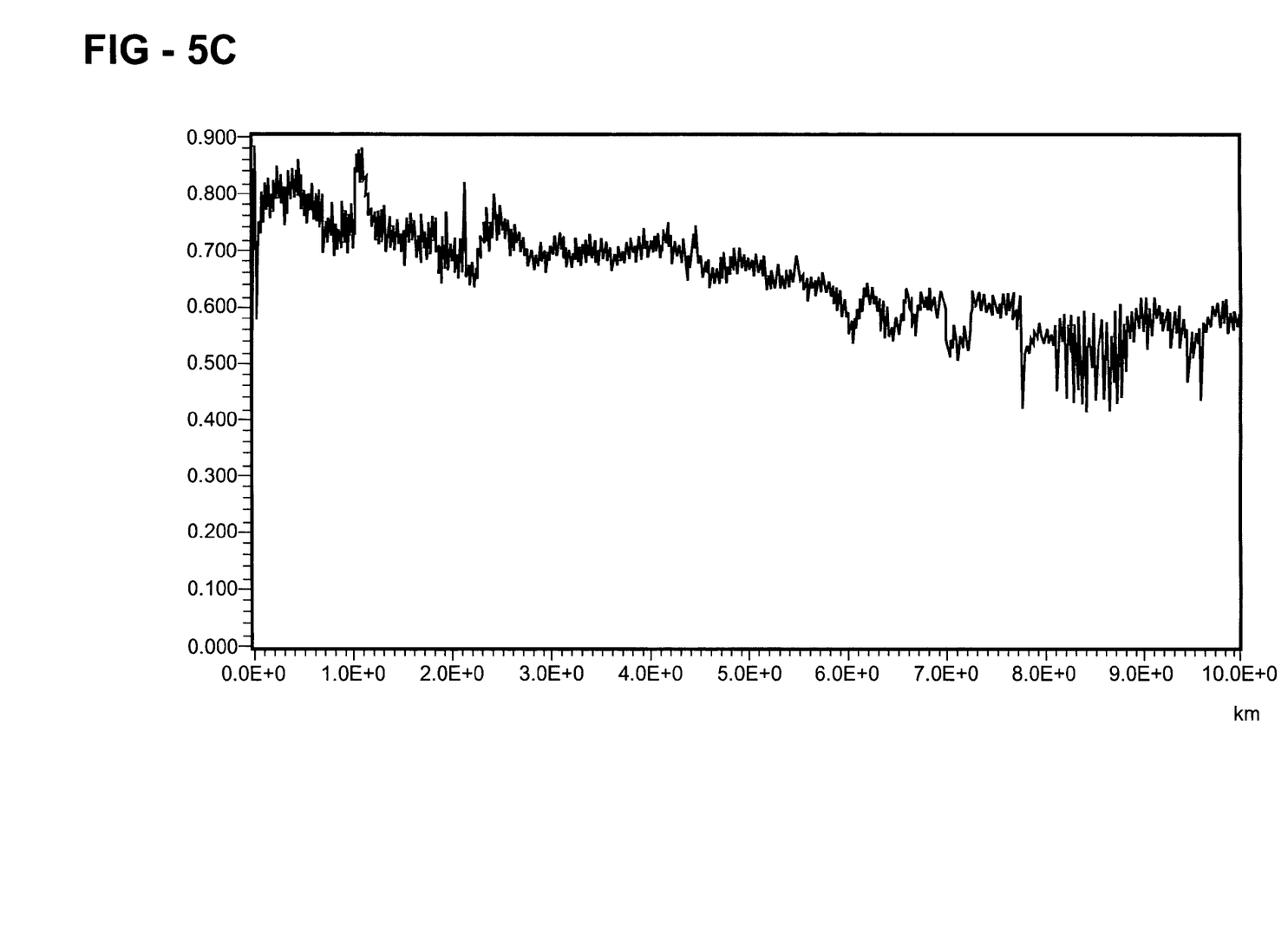
Figure 6A:
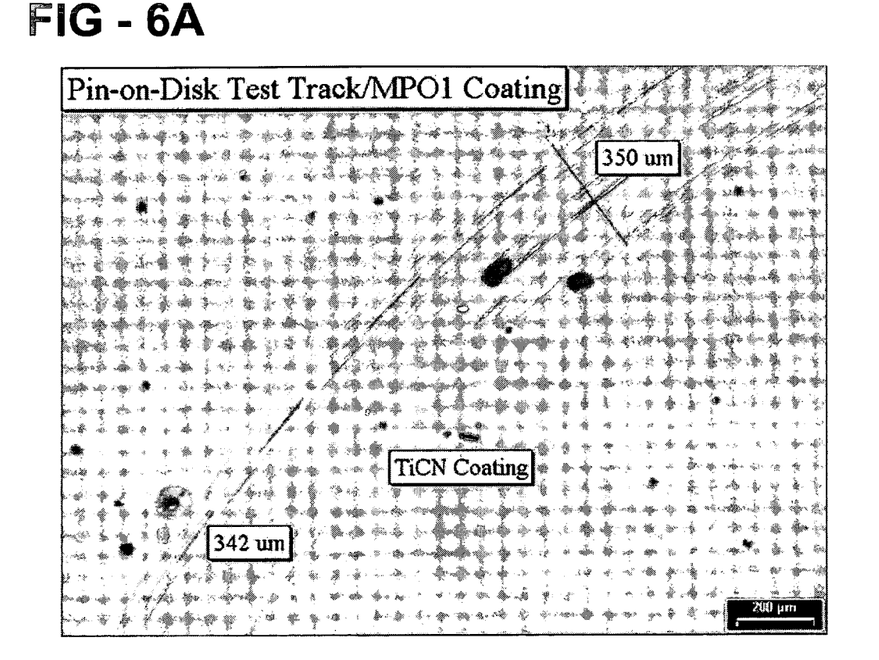
FIGS. 6A-6C are optical micrographs showing the wear track of the respective coatings of FIGS. 2A-2C.
Figure 6B:
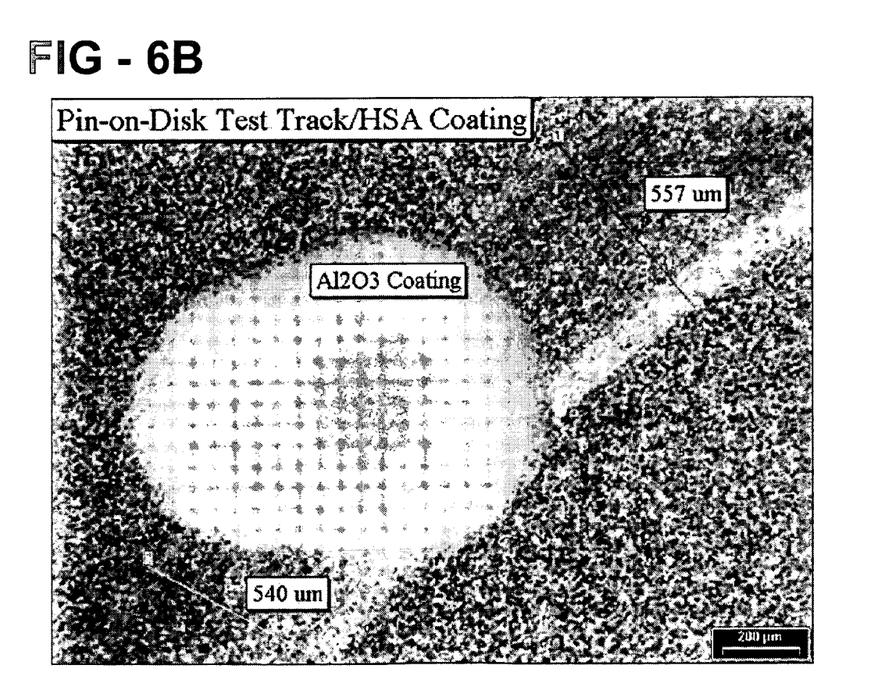
Figure 6C:
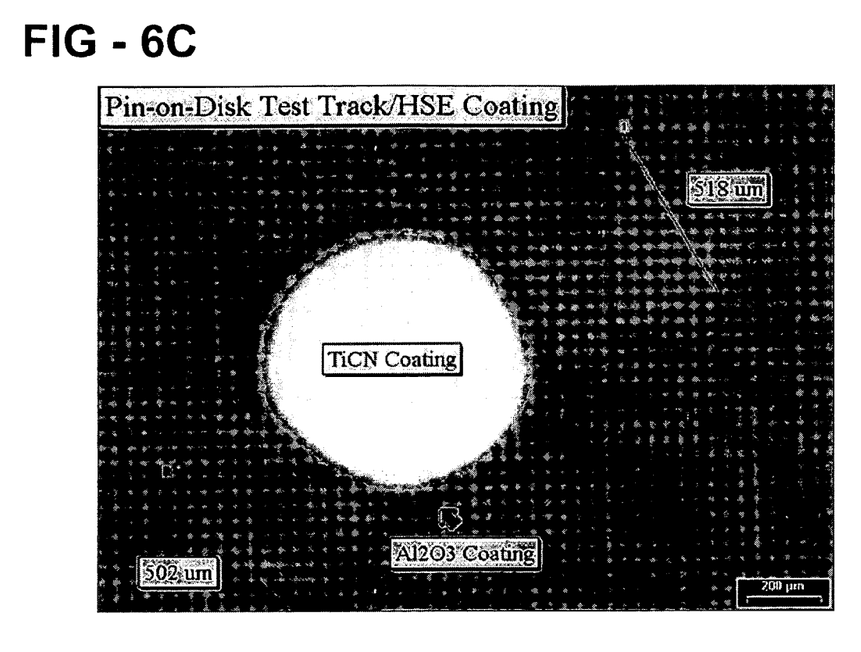
Figure 7A:
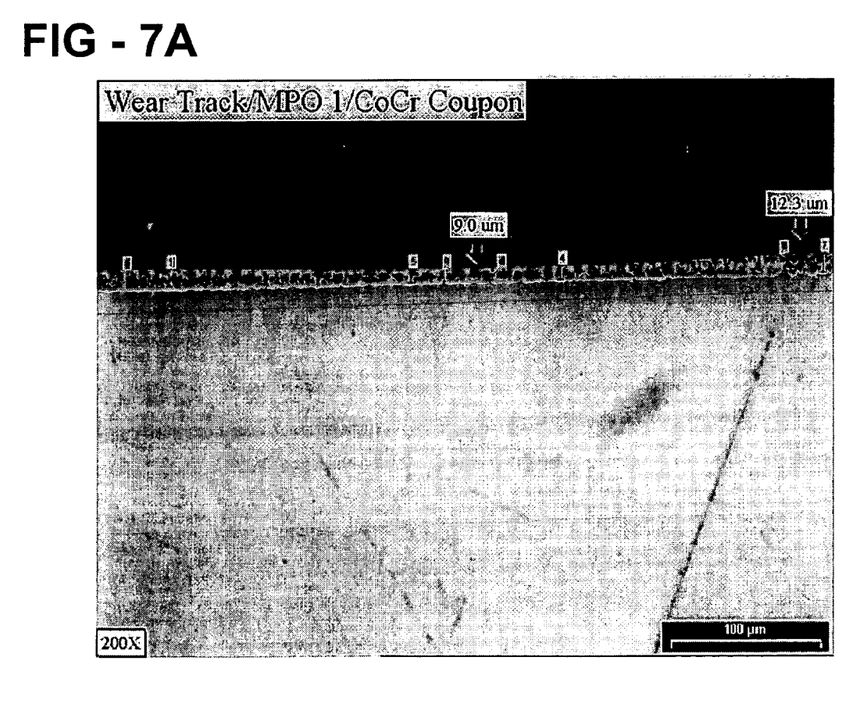
FIGS. 7A-7B are optical micrographs showing the cross-section of the wear track of FIG. 6A at different magnifications.
Figure 7B:
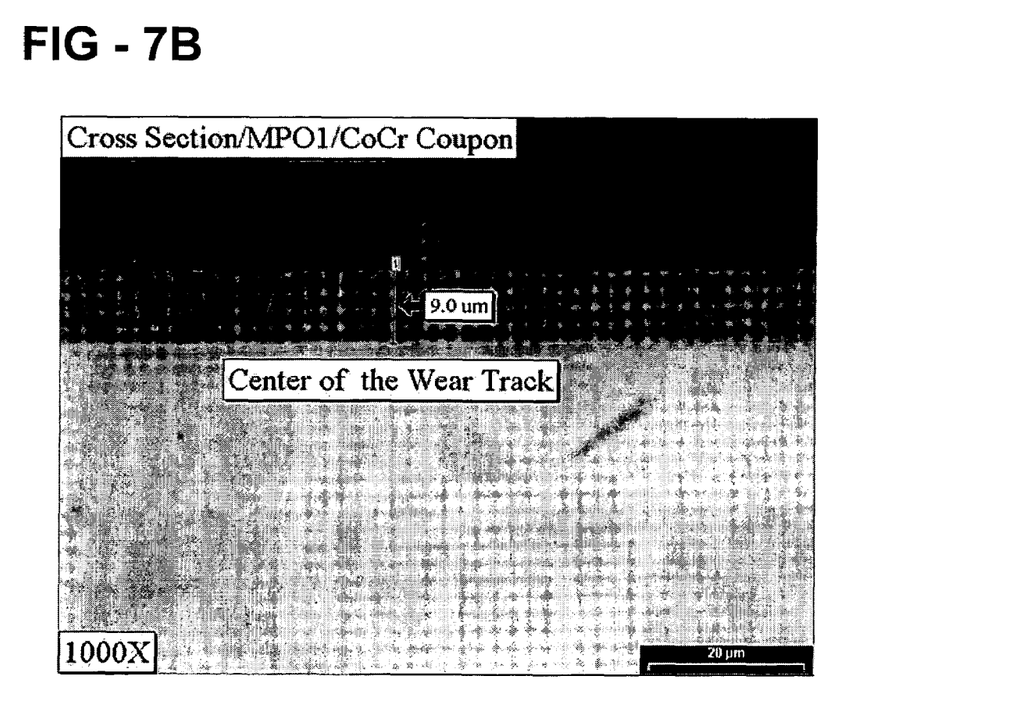

In order to evaluate the coating tribological properties, the pin-on-disc test was performed on the three coated substrates. The test load was 10N, the counterpart was 6 mm diameter WC ball, and the running distance was 10 km. FIGS. 5A-5C show the respective friction coefficient versus distance curves, and FIGS. 6A-6C show wear tracks after pin-on-disc test. The mean friction coefficient of the single species titanium carbonitride coating was about 0.13. In contrast, the mean friction coefficients for the two dual layer coatings were, respectively, approximately 0.68 and approximately 0.58. In all three cases, there still was titanium carbonitride or aluminum oxide coating left in the tracks after the completion of the tests. The cross-section of the wear track through the single species titanium carbonitride coating is shown in the optical micrographs of FIGS. 7A and 7B. As can be seen, a significant portion of the single species coating still exists after the test was complete.

In all three cases, the substrate was comprised of 65-weight percent cobalt, 30-weight percent chromium and 5-weight percent molybdenum.

The medical implant, coating and method of the present invention have the special advantages over the prior art of achieving a multi-layer coating which, due to the graded interface between the two ceramic layers, is particularly resistant to delamination. Furthermore, the underlying ceramic layer (the one that goes atop the substrate) can be chosen to be particularly adherent to the substrate through diffusion bonding and minimization of substrate alloy dissolution, whereas the upper layer can be selected to have particularly high hardness and good wear characteristics. Thus, it is possible to achieve in the dual layer structure of the present invention what cannot be achieved in the single layer coatings of the prior art, where there will always be a tradeoff in material selection between good adhesion versus high hardness and wear characteristics. However, because of the way the coating of the present invention is deposited, it is not prone to delamination, as we would normally expect from a conventional dual layer structure.

It should be noted that although in some instances certain materials are referred to by chemical formulas (e.g., $Al_2O_3$, TiCN, etc.), this is not meant to imply that these materials are of that precise stoichiometry. In some instances, depending on deposition conditions and the like, materials may deviate from nominal stoichiometry. In addition the aluminum oxide layer can be of either kappa alumina, alpha alumina or a mixture which includes layered structures of each. The present invention has been described with regard to certain embodiments and exemplifications thereof. However, it is to be understood that one of skill in the art, through routine experimentation, may find other exemplifications and embodiments suitable for the uses for which the present invention may be applied without departing from the practice of the present invention. Accordingly, it is the claims appended hereto, as well as all reasonable equivalents, rather than the exact depicted embodiments and exemplifications which define the true scope of the present invention.

The invention claimed is:

1. A medical implant comprising:
   a biologically compatible substrate; and
   a dual layered structure vapor deposited on at least a portion of the substrate, said dual layered structure comprising:
   a first ceramic layer in contact with said portions of said substrate; and
   a second ceramic layer in contact with said first ceramic layer;
   wherein said first and second ceramic layers are deposited in such a fashion so as to produce a graded interface between said first and second layers, said graded interface comprising a region including both the ceramic species of the first ceramic layer and the ceramic species of the second ceramic layer, said graded interface having a toothed, interlocking structure.

2. The medical implant of claim 1 wherein the substrate is comprised of CoCr medical grade alloy.

3. The medical implant of claim 1 wherein said first ceramic layer is comprised of titanium carbonitride.

4. The medical implant of claim 1 wherein said second ceramic layer is comprised of aluminum oxide.

5. The medical implant of claim 4 wherein the second layer comprises kappa alumina.

6. The medical implant of claim 4 wherein the second layer comprises alpha alumina.

7. The medical implant of claim 4 wherein the second layer comprises a mixture of a layered structure of both alpha and kappa alumina.

8. The medical implant of claim 1 wherein said first ceramic layer has a first thickness which is greater than a second thickness of said second ceramic layer.

9. The medical implant of claim 8 wherein said first thickness is in the range of 3-50 micrometers.

10. The medical implant of claim 8 wherein said second thickness is in the range of 0.5-15 micrometers.

11. The medical implant of claim 1 wherein the first layer has a graded composition.

12. The medical implant of claim 1 wherein the first layer inhibits diffusion of substrate material in the second layer.

13. A composition for coating a medical implant, said composition comprising a dual layered structure vapor deposited on at least a portion of said medical implant, said dual layered structure consisting essentially of:
   a first ceramic layer in contact with said portions of said substrate;
   a second ceramic layer in contact with said first ceramic layer; and
   wherein said first and second ceramic layers are deposited in such a fashion so as to produce a graded interface between said first and second layers, said graded interface comprising a region including both the ceramic species of the first ceramic layer and the ceramic species of the second ceramic layer, said graded interface having a toothed, interlocking structure.

14. The composition of claim 13 wherein said first ceramic layer is comprised of titanium nitride.

15. The composition of claim 13 wherein said second ceramic layer is comprised of aluminum oxide.

16. The composition of claim 13 wherein said first ceramic layer has a first thickness substantially greater than a second thickness of said second ceramic layer.

17. The composition of claim 16 wherein said second thickness is in the range of 0.5-15 micrometers.

18. The composition of claim 13 wherein said first thickness is in the range of 3-50 micrometers.

19. The composition of claim 13 wherein the second layer comprises kappa alumina.

20. The composition of claim 13 wherein the second layer comprises alpha alumina.

21. The composition of claim 13 wherein the second layer comprises a mixture of both alpha and kappa alumina.

22. The composition of claim 21, wherein said mixture comprises a layered structure.

23. The composition of claim 13 wherein the first layer has a graded composition.

24. The composition of claim 13 wherein the first layer inhibits diffusion of coating material in the substrate and avoids diffusion of substrate material in the second layer.

25. A medical implant comprising:
   a biologically compatible substrate; and
   a dual layered structure vapor deposited on at least a portion of the substrate, said dual layered structure comprising:
   a first titanium-based ceramic layer consisting of: titanium nitride or titanium carbonitride, in contact with said portions of said substrate; and
   a second ceramic layer in contact with said first ceramic layer;
   wherein said first and second ceramic layers are deposited in such a fashion so as to produce a graded interface between said first and second layers, said graded interface comprising a region including both the ceramic species of the first ceramic layer and the ceramic species of the second ceramic layer.

26. The medical implant of claim 25, wherein said second ceramic layer is an aluminum-based ceramic layer.

27. A medical implant comprising:
   a biologically compatible substrate; and
   a dual layered structure vapor deposited on at least a portion of the substrate, said dual layered structure comprising:
   a first ceramic layer in contact with said portions of said substrate; and
   a second aluminum oxide ceramic layer in contact with said first ceramic layer;
   wherein said first and second ceramic layers are deposited in such a fashion so as to produce a graded interface between said first and second layers, said graded interface comprising a region including both the ceramic species of the first ceramic layer and the ceramic species of the second ceramic layer.

* * * * *